March 23, 1976 A. W. FISCHER Plant Pat. 3,848
AFRICAN VIOLET NAMED
HELGA
Filed March 27, 1975
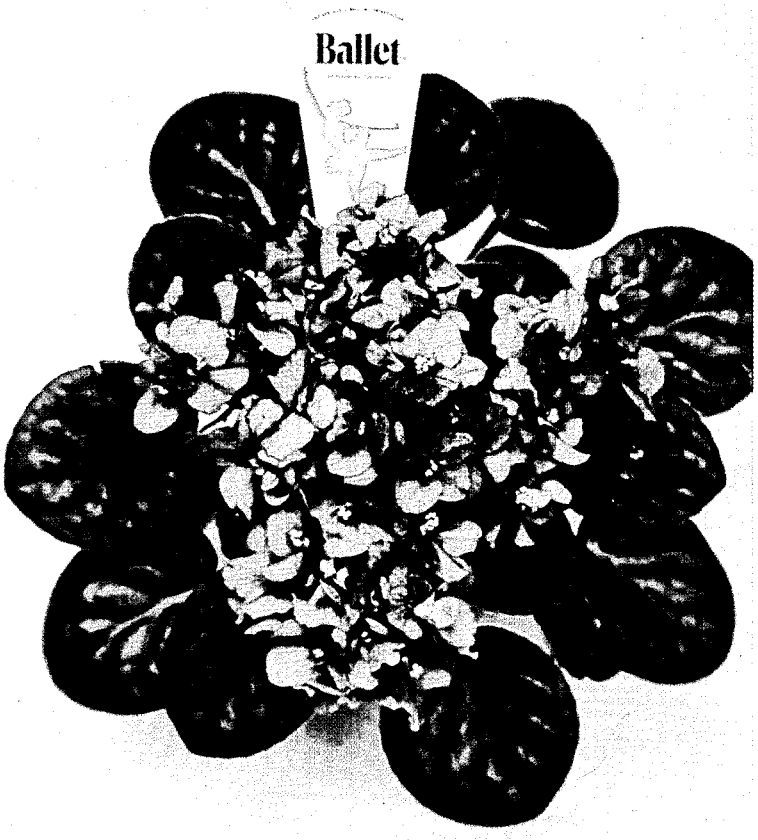

United States Patent

Plant Pat. 3,848

Patented Mar. 23, 1976

3,848

AFRICAN VIOLET NAMED HELGA

Arnold W. Fischer, Isernhagen, Germany, assignor to Geo. J. Ball, Inc., West Chicago, Ill.

Filed Mar. 27, 1975, Ser. No. 562,940

Int. Cl. A01h

U.S. Cl. Plt.—69 1 Claim

ABSTRACT OF THE DISCLOSURE

A new variety of African violet plant for potted plant culture distinguished by an improved growing and flowering performance and a long-lasting flowering cycle, the flowers having a distinctive rich violet purple color and being borne on upright peduncles so that the flowers form a dense canopy over the center of the plant, and the leaves having petioles which spread horizontally to provide a dark green collar for the flower mass.

BACKGROUND OF THE NEW PLANT

This new African violet plant was originated as a seedling resulting from a cross, made by me, of two unnamed and unpatented varieties selected from the stock of violet plants maintained by me at Isernhagen, Germany, with the object of producing a new flower color and a plant having improved growing and flowering performance. This new plant was selected by me for trial because of its novel color and vigorous growth and profuse flower production and subsequent asexual propagation by leaf cuttings, carried on by me and under my direction at Isernhagen, Hanover, Germany, has demonstrated that from generation to generation, the distinctive features of the plant hold true and appear to be firmly fixed. Propagation of this new plant on a commercial scale is now being carried on at West Chicago, Ill., U.S.A., by means of leaf cuttings and division of roots.

DESCRIPTION OF THE DRAWING

My new variety of African violet plant is illustrated by the accompanying photographic drawing which shows in full color the characteristics of the blossoms and foliage of the plant, as well as the form of the plant in full bloom, the color rendition being as nearly true as it is reasonably possible to obtain through conventional photographic procedures.

DESCRIPTION OF THE NEW PLANT

The following is a detailed description of this new African violet plant with the color designations being stated according to the Horticultural Colour Chart (HCC) developed for and published by the British Colour Council in collaboration with The Royal Horticultural Society at London, England.

THE PLANT

Origin: Seedling.

Parentage:

*Seed parent.*—069–13. *Pollen parent.*—66–1. Both parents are unnamed and unpatented varieties maintained for breeding purposes and identified in my permanent records by the stated numbers.

Classification:

*Botanic.*—Saintpaulia Ionantha.

*Commercial.*—African violet.

Form: Compact potted plant.

Height: Up to 4 inches from soil to top of flowers.

Growth: Condensed and vigorous with fairly strong petioles which tend to spread horizontally for a planar-like display of the foliage.

Foliage: Quantity—abundant.

*Size of leaf.*—About 3 inches long and 2¾ inches wide.

*Shape of leaf.*—Ovate to orbicular with smooth margins.

*Texture.*—Leathery and tomentose.

*Color.*—Upper side—Ivy Green 0001060/1. Under side—Sage Green 000861/3.

*Ribs and veins.*—Pronounced on under side of leaf.

*Petioles.*—Length—2½ to 3 inches. Color—Garnet Brown 00918/3.

THE BUD

Form: Globular, becoming urn-shaped as it opens.

Size: 5/16 inch in diameter.

Opening rate: 4 to 5 weeks from visible bud to opening of flower.

Color: When sepals first divide—Imperial Purple 33. When petals begin to unfurl—Imperial Purple 33/2. (The colors stated are a general representation of appearance as bud opens.)

Sepals: 5, hooded over bud for a short period.

*Color.*—Inside—Fern Green 0862/3. Outside—Garnet Brown 00918/3.

Calyx: Shape—pear-shaped.

*Size.*—Small.

*Splitting.*—Calyx splits with the 5 sepals making a star formation.

*Aspect.*—Hairy.

Pedicile: Length—½ to 1 inch.

*Aspect.*—Hairy.

*Color.*—Maroon 1030 ( a general representation).

THE FLOWER

Blooming habit: Profuse, recurrent the year around.

Size of flower: Medium. Diameter—about 1¾ inches.

Borne: In cluster. The inflorescense is a cyme.

Shape: Cup-shaped when first opening, becoming flat as flower opens full.

Petalage: Five, plus occasional petaloids.

*Arrangement.*—Sympetalous.

*Form.*—Rotate with bilateral symmetry. Semidouble in appearance due to occasional petaloids.

*Color.*—In general representation: Outer petals—Violet Purple 733/2. Inside petals—Violet Purple 733. Reverse sides—Imperial Purple 33/3 with darker margins 33/2.

*Appearance.*—A glittery upper surface and shiny under surface.

*Petaloids.*—Number—3 to 5. Size—small. Color: Violet Purple 733, in general. The petaloids seem more recurrent in subsequent flowerings as the plant becomes older.

Peduncle: Length—2 to 3 inches.

*Strength.*—Sturdy and upright.

*Color.*—Garnet Brown 00918/3.

Discoloration: Little change after full bloom. Imperial Purple 33/1 in general appearance.

Effect of Weather: Extreme hot weather adversely affects flowering.

Persistence: Flowers hang on and dry.

Fragrance: None.

Lasting quality: 10 to 14 days for fully opened flower.

REPRODUCTIVE ORGANS

Stamens: Irregular, usually 2, occasionally 3 to 5.

*Anthers.*—Two in number in basifixed arrangement, each with two anther cells, lemon yellow in color.

*Filaments.*—Appropimately ⅛ inch long.

*Pollen.*—Color—Naples Yellow 403.

Pistils: One only.

*Style.*—¼ inch long.

*Stigma.*—Color—in general, Violet Purple 733.

Ovaries: Typical of African violets.

The predominant characteristics of this new plant reside in its unique and distinctive violet purple coloring of the flowers, its vigorous growth, and the prolific production of flowers borne in clusters in sturdy, upright stems. This variety has the further advantage of year around flowering in recurrent, long-lasting flowering cycles, each of which produces a compact and centered mass of blossoms above the spreading foliage of the plant.

I claim:

1. A new variety of African violet plant, substantially as herein shown and described, characterized by its profuse production of flower clusters borne on sturdy, upright stems growing compactly at the center of the plant and surrounded by abundant, relatively large leaves carried on strong, horizontally-spreading petioles whereby the flowers form a dense canopy at the center of the plant and above the spreading foliage.

No references cited.

ROBERT E. BAGWILL, Primary Examiner